US012629091B2

(12) United States Patent
    Fichman et al.

(10) Patent No.: US 12,629,091 B2
(45) Date of Patent: May 19, 2026

(54) DEVICE, A SYSTEM, AND A METHOD FOR MONITORING BONE DENSITY AND A METHOD FOR IMPLANTING A DEVICE FOR MONITORING BONE DENSITY

(71) Applicant: Stichting IMEC Nederland, Eindhoven (NL)

(72) Inventors: Mark Fichman, Eindhoven (NL); Erfan Sheikhi, Eindhoven (NL); Seulki Lee, Eindhoven (NL); Navid Shahriari, Rotterdam (NL)

(73) Assignee: STICHTING IMEC NEDERLAND, Eindhoven (NL)

( * ) Notice: Subject to any disclaimer, the term of this patent is extended or adjusted under 35 U.S.C. 154(b) by 609 days.

(21) Appl. No.: 17/991,136

(22) Filed: Nov. 21, 2022

(65) Prior Publication Data

US 2023/0157628 A1     May 25, 2023

(30) Foreign Application Priority Data

Nov. 25, 2021    (EP) ..................................... 21210453

(51) Int. Cl.
    *A61B 5/00* (2006.01)
    *A61B 5/053* (2021.01)
    *A61B 8/00* (2006.01)
(52) U.S. Cl.
    CPC ............ *A61B 5/4509* (2013.01); *A61B 5/053* (2013.01); *A61B 8/4472* (2013.01)
(58) Field of Classification Search
    CPC ....... A61B 5/002; A61B 5/0031; A61B 5/053; A61B 5/0538; A61B 5/4509; A61B 5/6878; A61B 8/4472
    See application file for complete search history.

(56) References Cited

U.S. PATENT DOCUMENTS 7,907,998 B2    3/2011  Arad
8,131,354 B2    3/2012  Arad
                (Continued)

FOREIGN PATENT DOCUMENTS

WO    WO-2014/191991    12/2014

OTHER PUBLICATIONS

Balmer et al: "Characterization of the electrical conductivity of bone and its correlation to osseous structure", Scientific Reports, 8:8601, pp. 1-8, 2018.

(Continued)

*Primary Examiner* — Amanda K Hulbert

(74) *Attorney, Agent, or Firm* — MOSER TABOADA

(57)    ABSTRACT

A device for monitoring bone density comprises: a first electrode unit comprising a first electrode area to be arranged within a bone; a second electrode unit comprising a second electrode area to be arranged outside the bone, wherein the first and the second electrode units are configured for being arranged such that an electrical signal between the first and the second electrode areas travels through a cortical bone portion of the bone; an injection signal generating unit configured to provide an injection signal for generating the electrical signal; and a measurement unit configured to detect a measurement signal induced by the injection signal for determining an impedance between the first and the second electrode areas as a measure of bone density.

14 Claims, 10 Drawing Sheets

(56)                    References Cited

U.S. PATENT DOCUMENTS

| | | | |
|---|---|---|---|
| 2007/0238992 A1* | 10/2007 | Donofrio | A61B 8/56 |
| | | | 600/437 |
| 2009/0131838 A1 | 5/2009 | Fotiadis | |
| 2010/0326211 A1 | 12/2010 | Stein | |
| 2011/0213221 A1 | 9/2011 | Roche | |
| 2013/0296734 A1 | 11/2013 | Bourlion et al. | |
| 2017/0135671 A1 | 5/2017 | Nowak et al. | |
| 2020/0108252 A1 | 4/2020 | Zellmer et al. | |

OTHER PUBLICATIONS

Fujimoto et al: "Use of Bioelectrical Impedance Analysis for the Measurement of Appendicular Skeletal Muscle Mass/Whole Fat Mass and Its Relevance in Assessing Osteoporosis among Patients with Low Back Pain: A Comparative Analysis Using Dual X-ray Absorptiometry", Asian Spine Journal, vol. 12, No. 5, pp. 839-845, 2018 Öztürk et al: "Screening post-menopausal women for bone mineral level by bioelectrical impedance spectroscopy of dominant arm", Journal of Electrical Bioimpedance, vol. 9, No. 1, pp. 39-47, 2018.

Öztürk et al: "Screening post-menopausal women for bone mineral level by bioelectrical impedance spectroscopy of dominant arm", Journal of Electrical Bioimpedance, vol. 9, No. 1, pp. 39-47, 2018.

Kabala et al: "A new biosensor for osteoporosis detection", Preparative Biochemistry & Biotechnology, vol. 49, No. 5, pp. 511-520, 2019.

Lin et al: "Smart bone plates can monitor fracture healing", Scientific Reports, 9:2111, pp. 1-15, 2019.

Yoshida et al: "Measurement of bone electrical impedance in fracture healing"; Journal of Orthopaedic Science, vol. 14, No. 3, pp. 320-329, 2009.

Balmer et al: "In-Vivo Electrical Impedance Measurement in Mastoid Bone", Annals of Biomedical Engineering, vol. 45, No. 4, pp. 1122-1132, 2016.

Extended European Search Report in EP21210453.3 dated May 11, 2022.

* cited by examiner

Provide injection
signal for generating
electrical signal through
cortical bone portion — 402

Detect measurement
signal induced by
injection signal — 404

Determine impedance as a
measure of bone density — 406

2 pt

DEVICE, A SYSTEM, AND A METHOD FOR MONITORING BONE DENSITY AND A METHOD FOR IMPLANTING A DEVICE FOR MONITORING BONE DENSITY

CROSS-REFERENCE TO RELATED APPLICATIONS

The present application claims the benefit of and priority to EP Patent Application Serial No. 21210453.3, filed Nov. 25, 2021, the entire contents of which is incorporated herein by reference.

TECHNICAL FIELD

The present inventive concept relates to monitoring of bone density.

BACKGROUND

As human longevity increases, aging-associated diseases are becoming more common. Osteoporosis is an aging-associated disease causing a decrease of bone density and an increased risk of bone fractures. Prevalence of osteoporosis is a leading cause of disability and loss of independence among elderly people and increases with age.

There are typically no symptoms of osteoporosis until a bone fracture occurs. However, after bone fracture, a large proportion of elderly will not regain baseline level of independence.

Although common, osteoporosis is preventable and treatable. Diagnosis may typically be done with osteoporosis screening using X-ray and computed tomography (CT) scans. However, extensive screening of osteoporosis is difficult to implement using such technology. Thus, there is a need for a different technology allowing a process for screening for osteoporosis to be more accessible, which would increase frequency of screenings an improve early diagnosis of osteoporosis.

SUMMARY

An objective of the present inventive concept is to enable monitoring of bone density in a simple manner, such that screening for osteoporosis may be facilitated.

This and other objectives of the present inventive concept are at least partly met by the invention as defined in the independent claims. Preferred embodiments are set out in the dependent claims.

According to a first aspect, there is provide a device for monitoring bone density; said device comprising: a first electrode unit comprising a first electrode area and configured for arranging the first electrode area within a bone; a second electrode unit comprising a second electrode area and configured for arranging the second electrode area outside the bone, wherein the first electrode unit and the second electrode unit are configured for being arranged in relation to a cortical bone portion of the bone such that an electrical signal between the first electrode area and the second electrode area travels through the cortical bone portion of the bone; an injection signal generating unit configured to provide an injection signal for generating the electrical signal between the first electrode area and the second electrode area; and a measurement unit configured to detect a measurement signal induced by the injection signal for determining an impedance between the first electrode area and the second electrode area as a measure of bone density.

According to the present inventive concept, an impedance is used as a measure of bone density. The impedance can be easily measured based on detecting a measurement signal induced by an injected electrical signal through cortical bone. This implies that, compared to e.g. using X-ray or CT scans, the device does not require complex or expensive equipment for determining a measure of bone density.

It is an insight of the present inventive concept that a first electrode area should be arranged within a bone inside while a second electrode area should be arranged outside the bone. This implies that the electrical signal between the first electrode area and the second electrode area will be forced to travel through a portion of the cortical bone, such that the determined impedance represents the impedance of the cortical bone portion. It is a further insight of the present inventive concept that impedance of the cortical bone is substantially larger than impedance of soft tissue such that, unless the electrical signal is forced, by the arrangement of the first and second electrode areas, to travel through the cortical bone, the electrical signal may instead travel through soft tissue (even if a path is much longer through soft tissue). In order to enable use of a determined impedance as a measure of bone density, the electrical signal needs to travel through the cortical bone.

Thanks to the device being configured to allow arrangement of the first electrode area within the bone and a second electrode area outside the bone, the device is configured to detect the measurement signal so as to provide a measure of bone density. It is further realized that, a decrease in bone density results in a reduced impedance of the cortical bone portion, such that the determined impedance may be used as a measure of bone density.

The device may be used for monitoring bone density of a subject, which may be a living being, human or animal. However, it should be realized that the device may alternatively be used for monitoring bone density external to a subject, in vitro, or for monitoring bone density of artificial bones.

The determined impedance may provide an intermediate result, which may be further processed in order to determine whether the subject suffers from osteoporosis or another disease related to bone density.

The device may be configured to provide continuous monitoring of bone density, e.g. for continuous monitoring of the subject. This implies that the subject need not visit a hospital each time a screening for osteoporosis is to be made. Hence, a process for monitoring bone density is vastly improved, such that early detection of osteoporosis may be enabled. This may be used for improving life quality of subjects, since osteoporosis is preventable and treatable, once diagnosed.

Osteoporosis treatments today are statistical-based and typically comprise lifestyle changes and drug intake in order to slow down the deterioration of bone density. The device for monitoring bone density facilitates continuous monitoring of the bone density, which could also be used as input for applying a more patient-specific treatment. Thus, after osteoporosis has been diagnosed, even if diagnosed using other measurements without use of the device according to the first aspect, the device may still be used to allow a more frequent scanning of progress of bone density and effectively quantify efficiency of different treatments for the patient. As a result, the device may also provide input allowing reduction of the amount of (different kinds of)

drugs to be used for the patient and/or allowing guidance to be provided for ensuring that desired diet and lifestyle is followed by the patient. In addition, the monitoring of the bone density may allow obtaining data for understanding relations between diet, lifestyle and/or drug intake and bone density, which may be used in future treatment of the patient and/or other patients. For instance, understanding of effect of sudden changes in diet may be obtained. Also, understanding of effect of food intake at different times of day may be obtained. Such understanding may be used in improving future efficiency of treatment for the patient.

The injection signal may be a current signal or a voltage signal. If a current signal is used for the injection signal, the measurement unit may detect a voltage signal for determining the impedance. If a voltage signal is used for the injection signal, the measurement unit may detect a current signal for determining the impedance.

The injection signal generating unit may be connected to the first electrode area and the second electrode area for providing the electrical signal between the first electrode area and the second electrode area. The measurement unit may also be connected to the first electrode area and the second electrode area for measuring a signal between the first electrode area and the second electrode area. Thus, the same electrode areas may be used both for injecting a signal and for measuring a signal. However, it should be realized that in other embodiments, separate electrode areas may be used for detecting the measurement signal.

A small amplitude of the injection signal may be used such that the injection signal will not cause any sensation or trigger any response in the subject. Rather, the injection signal should only be used for measuring the impedance between the first electrode area and the second electrode area. For instance, the amplitude of the injection signal may be so small that an activation threshold of a nerve is not exceeded.

Outer shell of compact bone is called cortical bone or cortex. The cortical bone surrounds soft, sponge-like bone tissue, which is internal tissue of skeletal bone. The device is configured to allow determining the impedance through at least a part of cortical bone, so as to relate the determined impedance to bone density. However, the device may in addition be configured to determine the impedance through cancellous bone.

The first electrode unit may be configured for arranging the first electrode area inside or within a cortical bone portion. Thus, the first electrode area may be arranged inside the cortical bone, e.g. in the soft, sponge-like bone tissue surrounded by the cortical bone. However, the first electrode area may alternatively be arranged within the cortical bone portion, such that the first electrode area is embedded in the cortical bone.

The second electrode unit is configured for arranging the second electrode area outside the bone, i.e. externally to the bone. This implies that at least part of a cross-section of the cortical bone is arranged between the first electrode area and the second electrode area when the device is used. Hence, the injection signal will travel through cortical bone between the first electrode area and the second electrode area.

It should be realized that the measurement signal may be used for determining a representation of the impedance between the first electrode area and the second electrode area. This may not necessarily imply that an actual impedance is determined. For instance, the measurement signal may be processed so as to determine an admittance, being reciprocal to the impedance, which may be used as the representation of the impedance for providing the measure of the bone density.

It should further be realized that the device may comprise additional pair(s) of electrode units, which are configured for arranging first electrode area of the pair of electrode units within a bone and configured for arranging second electrode area of the pair of electrode units outside the bone, wherein the pair of electrode units are configured for being arranged in relation to the cortical bone portion of the bone such that an electrical signal between the first electrode area and the second electrode area of the additional pair travels through the cortical bone portion of the bone. Further, the injection signal generating unit may be configured to provide an injection signal for generating the electrical signal between the first electrode area and the second electrode area of the additional pair of electrode units; and the measurement unit may be configured to detect a measurement signal induced by the injection signal for determining an impedance between the first electrode area and the second electrode area of the additional pair as a measure of bone density. Hence, measurements relating to bone density may be performed in plural target areas of one or more bones, such that several pairs of electrode units may allow obtaining more information on condition of bones.

According to an embodiment, the device further comprises a housing carrying the injection signal generating unit and the measurement unit.

This implies that the injection signal generating unit and the measurement unit may be arranged in a common housing facilitating handling of the device.

According to an embodiment, the device is configured to be fully implanted in a subject.

This implies that the device may be implanted in the subject and may thereafter be used for monitoring bone density. Hence, after implantation of the device, the device will always be carried by the subject and may be available at any time for performing measurements to provide indications of bone density of the subject.

The device comprising a housing carrying the injection signal generating unit and the measurement unit may be particularly useful when the device is to be fully implanted. In such case, during implantation, the housing will not to be placed within the subject and the first and second electrode units may further need to be separately placed within the subject and then connected to the housing. This arrangement of the device facilitates implantation of the device since few separate parts need to be implanted.

According to an embodiment, the first electrode unit comprises an elongate body configured to extend from the housing and a tip of the elongate body exposing a conductive portion forming the first electrode area.

The elongate body may be configured to allow at least part of the elongate body to extend within the cortical bone or inside the cortical bone. The elongate body may be configured to be inserted through an opening (that may be formed during implantation of the device) into the cortical bone. The elongate body may further extend within the bone such that the tip of the elongate body may be arranged at a distance from the opening. This may ensure that the electrical signal travels through the cortical bone portion instead of through the opening into the cortical bone.

The elongate body may be configured to allow the tip of the elongate body to be arranged at a distance from the opening being at least 1 cm, such as at least 5 cm. It should be realized that the arrangement of the elongate body within the bone may depend on which bone of the subject for which bone density is to be monitored. The device may be configured to be used for arrangement of the first electrode area and the second electrode area in a position which is particularly prone to bone fragility, such as a position in an upper part of femur for monitoring risk of hip fracture. A length of the elongate body may then be designed based on appropriate access into the cortical bone for arranging the first electrode area in a desired position.

The elongate body may further be configured to be connected to the housing for connecting the first electrode unit to the housing. Thus, the elongate body may further be configured to extend from a location of the housing to the opening into the cortical bone.

The elongate body may be flexible in order to allow the elongate body to be guided into position. The elongate body may be configured to extend from a first end to a second end, wherein the first end is configured to be connected to the housing and wherein the tip is arranged at the second end.

The elongate body may comprise a conductive line extending within the elongate body. The elongate body may further comprise an insulating casing surrounding the conductive line so as to ensure that the electrical signal leaves the first electrode unit through the first electrode area at the tip of the elongate body.

The first electrode area at the tip of the elongate body may be designed to facilitate a desired electrical signal to travel between the first electrode area and the second electrode area. The first electrode area may have a dimension to allow a strong signal to be formed. For instance, the first electrode area may be at least 1 cm$^2$. However, it should be realized that a suitable size of the first electrode area may depend on the position in which the first electrode area is to be arranged and that different sizes of the first electrode area are conceivable. For instance, a smaller size of the first electrode area, such as a first electrode area of at least 1 mm$^2$ may be used.

According to an embodiment, the tip has a directional shape for promoting the electrical signal being directed towards or being received from the second electrode area.

Thus, the device may be configured to allow the elongate body to be arranged in the bone so as to allow the tip to be arranged for directing the electrical signal towards the second electrode area. This may facilitate detection of a strong measurement signal so as to allow robust determination of the impedance between the first electrode area and the second electrode area.

The tip may for instance be formed as a cylinder, wherein only half of the cylinder is conductive for defining the first electrode area, which would imply that the tip promotes an electrical signal to be directed in a particular direction.

According to an embodiment, the conductive portion comprises a conductive wire arranged in a helix.

This implies that the conductive wire may form a large electrode area in a small volume.

The conductive line may extend out of the casing of the elongate body at the tip so as to expose the conductive line at the tip of the elongate body. Thus, the conductive line may form the first electrode area at the tip of the elongate body.

According to an embodiment, the housing and the first electrode unit each comprise fixation structures for fixating the housing and the first electrode unit, respectively, in relation to the bone.

The housing and the first electrode unit may be fixated in the body of the subject so as to prevent migration risks. The fixation structures may allow for a firm fixating of the housing and the first electrode unit. It should be realized that any type of fixation structures could be used for ensuring that the housing and the first electrode unit are fixed. For instance, screws may be used for fixating the housing and the first electrode unit to the bone. According to other alternatives, hooks, barbs, or any other structures that may engage with tissue or the bone may be used for fixating the housing and the first electrode unit, respectively.

The second electrode unit may be similar or even identical to the first electrode unit. Thus, the description provided above in relation to the first electrode unit may also apply to the second electrode unit. In particular, the second electrode unit may also comprise an elongate body configured to extend from the housing and a tip of the elongate body exposing a conductive portion forming the first electrode area.

Further, the tip of the elongate body of the second electrode unit may have a directional shape for promoting the electrical signal being directed towards or being received from the first electrode area. Also, the conductive portion of the second electrode unit may comprise a conductive wire arranged in a helix. Further, the second electrode unit may comprise fixation structures for fixating the second electrode unit in relation to the bone.

According to an alternative, the second electrode unit comprises a conductive portion arranged on an external wall of the housing for forming the second electrode area.

Hence, the second electrode area may be arranged directly on the housing. This implies that the second electrode area need not be separately positioned in the subject but may rather be arranged in a proper position when the housing is positioned in the subject.

The second electrode area may be connected to internal components in the housing directly through the wall at which the second electrode area is arranged, such that a connection to the second electrode area through the wall of the housing is not exposed.

According to an alternative, the device is configured to be powered through wireless power transfer.

This implies that the device may be powered through wireless power transfer each time an impedance measurement is to be performed. The functionality of the device may thus be maintained over a very long period of time, so as to enable the device to be permanent and avoiding or significantly reducing a risk of any need of further surgery to repair or replace parts of the device once the device has been implanted.

The wireless power transfer may transmit energy to the device using electromagnetic fields. The wireless power transfer may for instance use inductive or capacitive coupling for providing power to the device. The wireless power transfer may alternatively use emitted beams, such as radio frequency waves.

According to another embodiment, the device comprises a battery which is configured to be wirelessly charged.

This implies that the device may be fully implanted in the subject and may be battery-powered for being operational. The battery being wirelessly chargeable implies that the battery may be charged from an external unit, which is arranged externally to the subject when the battery is charged. This implies that the device may be fully implanted in the subject and may remain operational for a long period of time.

The battery may be configured to be wirelessly charged in a similar manner as described above for wireless power transfer for powering the device.

According to an embodiment, the device comprises a wireless communication unit for communicating measurement results to an external unit.

By communicating the measurement results to an external unit, presentation of the results to the subject or a caregiver is facilitated. The external unit may also further process the measurement results, e.g. for further analysis of the bone density.

Thanks to use of wireless communication, the device may be fully implanted, and results may still be accessible at the external unit.

The device may be configured to use a common technology for wireless power transfer and wireless communication, such that the battery may be wirelessly charged while the device communicates with the external unit.

The device may be configured to communicate measurement results continuously to the external unit. For instance, each time a measurement is performed, the measurement result may be communicated. However, according to an alternative, the device may be configured to only communicate measurement results when the measurement result has changed. Thus, the device may only communicate measurement results to the external unit as an indication that the bone density has deteriorated. For instance, the device may transmit an alert message indicating that further investigation of bone density or stage of osteoporosis is needed.

According to an embodiment, the injection signal generating unit is configured to provide at least one alternating current (AC) signal of one or more frequencies and/or a direct current (DC) signal.

An impedance measurement may thus be performed in an AC signal. The impedance measurement may be performed using any frequency for which a change in impedance may be seen based on a change in bone density. For instance, the impedance measurement may use one or more frequencies in a range of 1 kHz-1 MHz, such as 1-10 kHz. However, it should be realized that other frequencies may be used as well.

The measurement results of the impedance measurement may be analyzed based on an impedance at a particular frequency or based on a combination of impedances at a plurality of frequencies. For instance, an impedance spectroscopy measurement may be performed in order to acquire impedance measurements from a plurality of frequencies and allow analysis of the plurality of measurement results as a measure of bone density.

The impedance measurement may alternatively be performed in a DC waveform, using a discharging phase in order not to charge tissue between the first and the second electrode areas.

According to an embodiment, the device is configured to store a unique identifier related to the subject for which the device is used. Since the device is implanted in the subject, it will be available to medical staff. Hence, if there is an emergency situation, where the subject may not be conscious, the unique identifier may be pulled from the device to allow emergency caregivers to pull medical history of the subject. This may for instance be useful to avoid administrating drugs to the subject that may cause allergic reactions.

According to a second aspect, there is provided a system for monitoring bone density, comprising: the device according to the first aspect, wherein the device is configured to be fully implanted in a subject, the device being configured to be wirelessly powered and comprising a wireless communication unit for communicating measurement results; and an external reader unit, configured to emit a powering signal to the device and configured to receive a communication signal from the wireless communication unit of the device for receiving measurement results, wherein the external reader unit comprises a user interface for presenting measurement results to the subject.

Effects and features of this second aspect are largely analogous to those described above in connection with the first aspect. Embodiments mentioned in relation to the first aspect are largely compatible with the second aspect.

The implantable device and the external reader unit may form a kit that is adapted to perform impedance measurements for determining an impedance as a measure of bone density and to provide a user interface for viewing measurement results. The external reader unit may enable further user interaction, which may provide a control of the implanted device and/or may control processing of the measurement results.

For instance, the external reader unit may be used for allowing a user to control how often measurements are to be performed. The external reader unit may further be used for processing the measurement results and a user may control the processing to be performed.

According to an embodiment of the device, the device is configured to store historical measurement results of the impedance of a subject and to compare measurement results to the historical measurement results for identifying a change in the determined impedance for the subject.

According to an embodiment of the system, the system is configured to store historical measurement results of the impedance of a subject and to compare measurement results to the historical measurement results for identifying a change in the determined impedance for the subject.

It should be realized that the device may merely store historical measurement results, whereas processing of the measurement results may be performed in the external reader unit of the system or in another part of the system. Further, the device need not store any historical measurement results, but these may instead be stored in the external reader unit or in any other part of the system. Further, it should be understood that processing of measurement results may be distributed between different parts of the system, so as to be partly performed in different parts, such as the device and the external reader unit.

Thus, the device (or some other part of the system) may store one or more historical measurement results as reference to new measurements. By comparing measurement results to historical measurement results, the device (or some other part of the system) may identify impedance changes for the subject. The impedance changes may be an indication of deterioration of bone density, such that the device (or some other part of the system) may trigger transmission of an alert message when a change in the determined impedance is identified.

The identifying of the change in the determined impedance may be based on a threshold in relation to the historical measurement results, such that a change may only be identified if the measurement results differ substantially from the historical measurement results.

By using a comparison to historical measurement results of the subject, the monitoring of bone density may be personalized. This implies that the device or the system may provide a monitoring of bone density that is adapted to the subject for which the device is used.

The measurement results may be transmitted from the device without any processing of the measurement results being performed in the device. The measurement results may thus for instance be transmitted to an external unit and the historical measurement results of the impedance of the subject may instead be stored in the external unit. This implies that measurement results may instead be processed in the external unit to compare the measurement results to the historical measurement results for identifying a change.

According to another embodiment, the device (or the external unit) is configured to store nominal measurement results of the impedance. The measurement results for the subject may thus be compared to the nominal measurement results for identifying impedance of the subject deviating from the nominal measurement results. Identifying deviations from the nominal measurement results may then be used as an indication that the bone density of the subject is low, and that further investigation of bone density or stage of osteoporosis is needed.

According to a third aspect, there is provided a method for monitoring bone density, said method comprising: providing an injection signal for generating an electrical signal between a first electrode area and a second electrode area, wherein the first electrode area and the second electrode area are arranged in relation to a cortical bone portion of a bone such that the electrical signal between the first electrode area and the second electrode area travels through the cortical bone portion of the bone; detecting a measurement signal induced by the injection signal; and determining an impedance between the first electrode area and the second electrode area as a measure of bone density.

Effects and features of this third aspect are largely analogous to those described above in connection with the first, and second aspects. Embodiments mentioned in relation to the first, and second aspects are largely compatible with the third aspect.

The method allows a continuous monitoring of the subject. This implies that the subject need not visit a hospital each time a screening for osteoporosis is to be made. Hence, a process for monitoring bone density is vastly improved, such that early detection of osteoporosis may be enabled.

The determined impedance may provide an intermediate result, which may be further processed in order to determine whether a subject suffers from osteoporosis or another disease related to bone density.

The method may be performed by an injection signal generating unit and a measurement unit, which may control the generation of the injection signal and may acquire measurement signals for determining the impedance.

According to a fourth aspect, there is provided a method for implanting a device for monitoring bone density, said method comprising: acquiring access to an interior of a bone; guiding a first electrode area of a first electrode unit at a tip of the first electrode unit into the interior of the bone for arranging the first electrode area of the first electrode unit within the bone; arranging a second electrode area of a second electrode unit outside the bone, wherein the first electrode unit and the second electrode unit are arranged in relation to a cortical bone portion of the bone such that an electrical signal between the first electrode area and the second electrode area travels through the cortical bone portion of the bone; arranging a housing in vicinity of the bone, wherein the housing is configured to carry an injection signal generating unit, configured to provide an injection signal for generating the electrical signal between the first electrode area and the second electrode area; and a measurement unit configured to detect a measurement signal induced by the stimulation signal for determining an impedance between the first electrode area and the second electrode area as a measure of bone density; and connecting the first electrode unit to the housing.

Effects and features of this fourth aspect are largely analogous to those described above in connection with the first, second, and third aspects. Embodiments mentioned in relation to the first, second, and third aspects are largely compatible with the fourth aspect.

The method enables simple implantation of the device so as to ensure that the device is properly implanted in the device for allowing monitoring of bone density.

The method may comprise acquiring access to an interior of the bone inside or within a cortical bone portion of the bone. The first electrode area may be guided for arranging the first electrode area inside or within the cortical bone portion of the bone.

BRIEF DESCRIPTION OF THE DRAWINGS

The above, as well as additional objects, features, and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
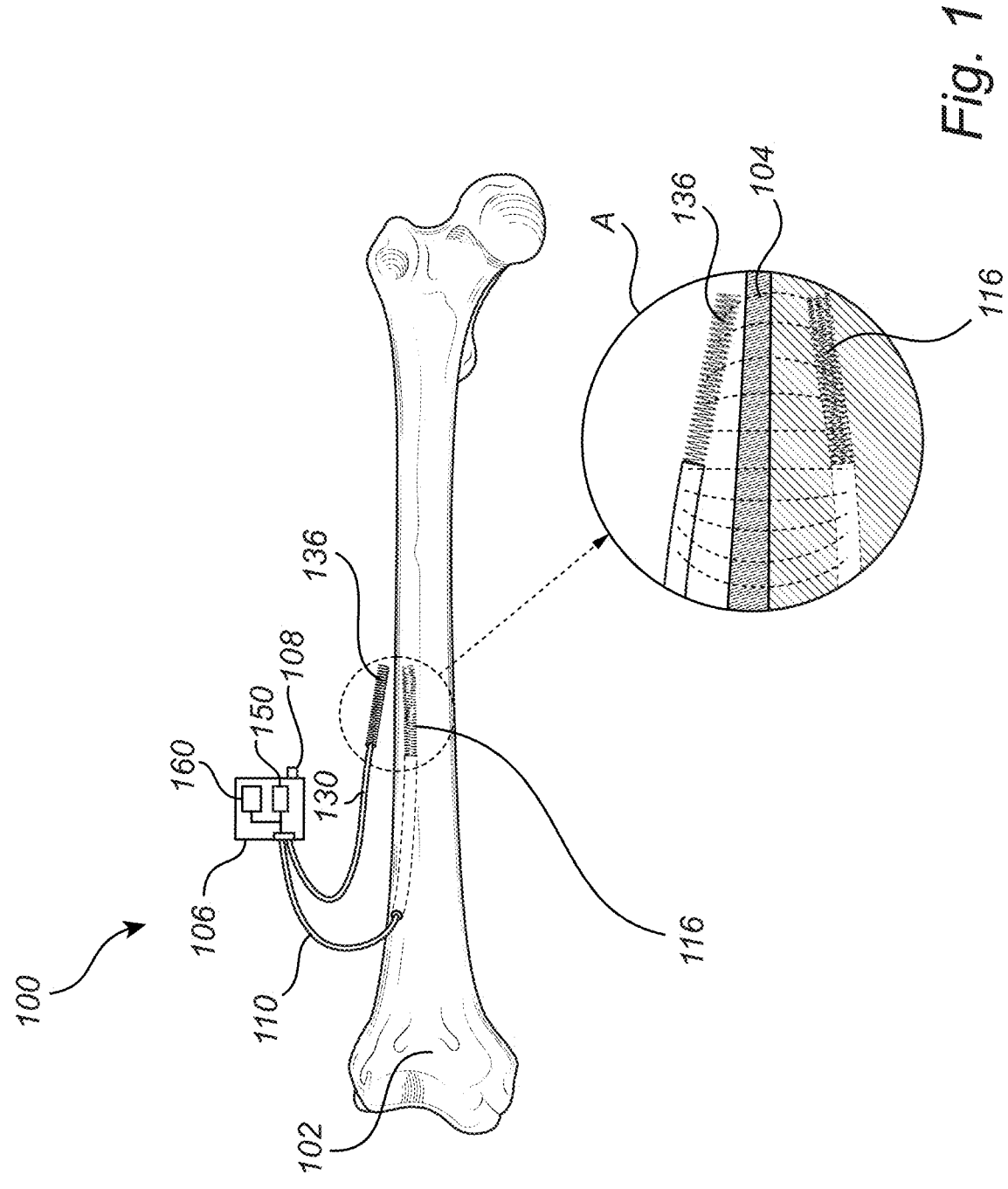
FIG. 1 is a schematic view of a device according to an embodiment.

Referring now to FIG. 1, a device 100 for monitoring bone density will be described. The device 100 is configured for arranging electrode areas in relation to a cortical bone for generating an injection signal causing an electrical signal to be transmitted through the cortical bone and detecting a measurement signal induced by the injection signal for determining an impedance related to the cortical bone. The device 100 is configured to use the determined impedance as a measure of bone density.

The device 100 enables determining the measure of bone density in a simple manner and the device 100 may be implanted in a subject to allow for continuous monitoring of the bone density of the subject. The device 100 may therefore advantageously be used for early detection of osteoporosis and may also be used for monitoring bone density during treatment of osteoporosis for finding a suitable treatment plan that is adapted to the specific subject.

The device 100 comprises a first electrode unit 110 and a second electrode unit 130. The first electrode unit 110 comprises a first electrode area 116 and the second electrode unit 130 comprises a second electrode area 136. The first and second electrode units 110, 130 are configured such that the first electrode area 116 and the second electrode area 136 can be arranged with a cortical bone portion 104 of a target bone 102 arranged between the first electrode area 116 and the second electrode area 136. Thus, the injection signal may cause the electrical signal to be transmitted through the cortical bone portion 104. The first electrode area 116 may be configured to be arranged within the bone 102 inside or within the cortical bone portion 104. The second electrode area 136 may be configured to be arranged outside the bone 102.

Figure 2:
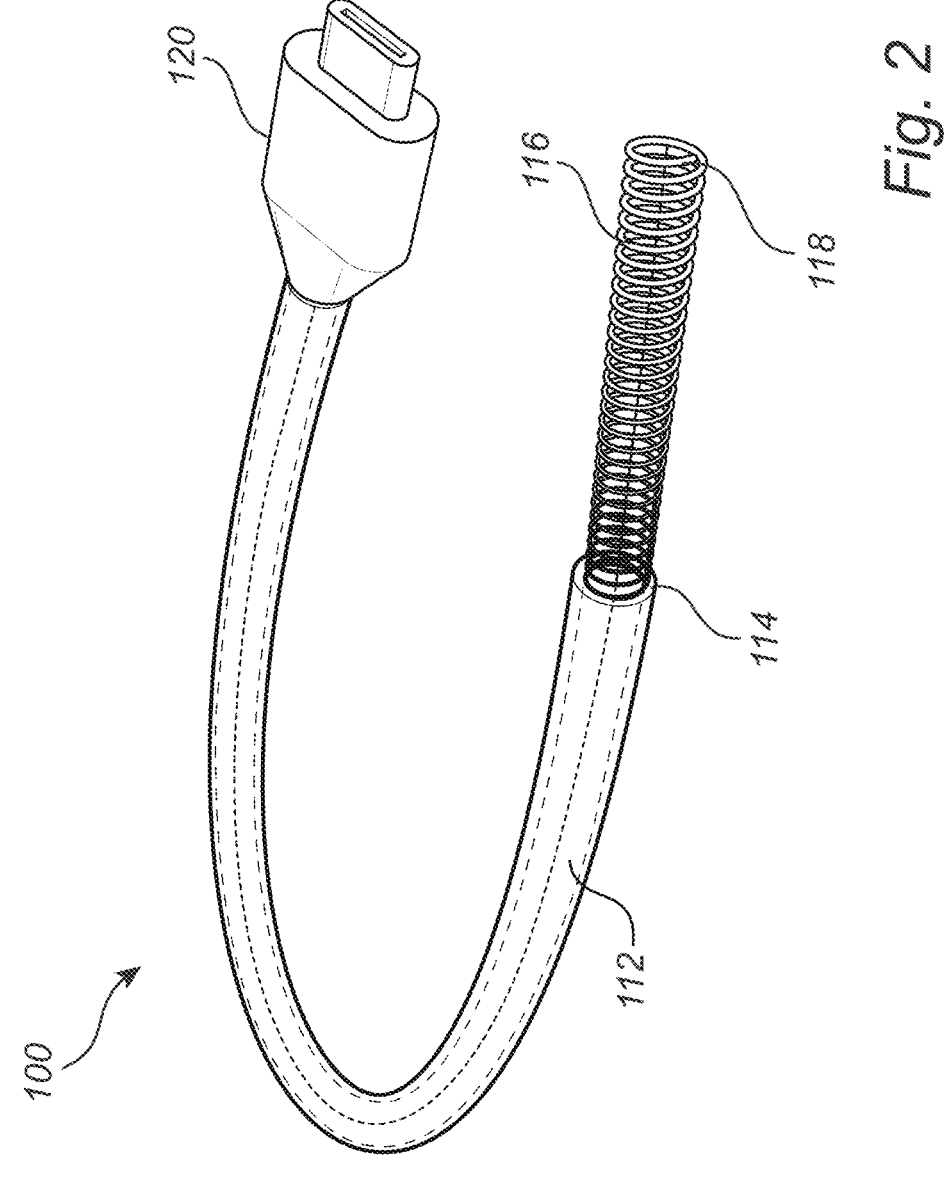
FIG. 2 is a schematic view of an electrode unit of the device.

Referring now to FIG. 2, the first electrode unit 110 will be described in greater detail. The second electrode unit 130 may have an identical design to the first electrode unit 110. Thus, it should be realized that the description of the first electrode unit 110 below may apply also to the second electrode unit 130.

The first electrode unit 110 may comprise an elongate body 112. The elongate body 112 may be flexible so that it may be bent to follow a desired path within the body of the subject. The first electrode unit 110 may further comprise a conductive wire, which may be carried by the elongate body 112 and may extend through the elongate body 112 for transferring an electrical signal through the elongate body 112. The elongate body 112 may further comprise an outer insulating casing 114, which may cover the conductive wire for ensuring that the electrical signal is transferred through the conductive wire and not coupled into tissue or any other surroundings around the elongate body 112.

The first electrode unit 110 further comprises the first electrode area 116. The first electrode area 116 may be formed at a tip 118 of the elongate body 112. The conductive wire may be exposed at the tip 118 for forming the first electrode area 116. As shown in the enlargement A in FIG. 1, the conductive wire may be arranged in a helix shape at the tip 118 for providing a large area of the first electrode area 116 at the tip 118 in a small volume. Thus, a strong coupling of signals between the first electrode area 116 and a second electrode area 136 of the second electrode unit 130 may be provided.

The first electrode area 116 may have a size of at least 1 mm², such as at least 1 cm². A relatively large size of the first electrode area 116 implies that positioning of the first electrode area 116 may not be very critical in order to ensure that the first electrode area 116 and the second electrode area 136 are arranged in a close relation to each other with the cortical bone portion 104 between the first electrode area 116 and the second electrode area 136.

The first electrode unit 110 may be configured to promote transmission/reception of electrical signals to/from a particular direction. This implies that the electrical signal to be transmitted between the first electrode area 116 and the second electrode area 136 may be relatively strong allowing a stronger measurement signal to be measured for a robust determination of the impedance.

The tip 118 of the elongate body 112 may have a directional shape for promoting the direction of the electrical signal. For instance, the tip may be formed as a cylinder, wherein only half of the cylinder is conductive for defining the first electrode area 116, which would imply that the tip 118 promotes the electrical signal to be directed in a particular direction of the conductive half of the cylinder.

The elongate body 112 may have a length allowing the elongate body 112 to extend along a relatively long path within the body of the subject. The first electrode unit 110 is configured such that the first electrode area 116 may be arranged within a bone 102 of the subject inside or within a cortical bone portion 104 of the bone 102. The first electrode unit 110 may be configured to be arranged to extend through an opening (e.g. formed by drilling into the bone 102) into the bone 102. The length of the elongate body 112 may further allow for the first electrode area 116 to be arranged at a distance from the opening into the bone 102. For instance, the elongate body 112 may extend a distance of at least 1 cm, such as at least 5 cm within the bone 102 for arranging the first electrode area 116 at a distance from the opening.

This implies that the electrical signal to be transmitted through the cortical bone portion 104 will actually pass through the cortical bone portion 104 instead of through the opening. Any risk of signals passing through the opening instead of through the cortical bone portion 104 may also decrease over time as the opening may be sealed through re-generation of bone tissue around the elongate body 112 extending into the bone 102.

The elongate body 112 may further have a length to allow the elongate body 112 to be connected to other components of the device 100, which are arranged outside the bone 102. The other components of the device 100 may for instance be arranged in a common housing 106 as described in further detail below. The elongate body 112 should thus have a length to allow the elongate body 112 to extend from the first electrode area 116, via the opening into the bone 102, to the housing 106. The elongate body 112 may have a length that is larger than required to extend along the desired path of the elongate body 112. Having a margin on the required length of the elongate body 112 may avoid problems when the device 100 is to be positioned in the body of the subject.

The second electrode unit 130 may be slightly shorter than the first electrode unit 110, since the second electrode unit 130 need not extend via an opening into the bone 102 and then further within the bone 102. Instead, the second electrode unit 130 may be configured to be arranged completely outside the bone 102.

It should be realized that the first electrode unit 110 may be formed in other manners, such as defining the first electrode area based on a continuous surface of a conductive material.

The first electrode unit 110 may further comprise a connector 120 for allowing the first electrode unit 110 to be connected to other electrical components of the device 100. The connector 120 may have a mating relationship to a corresponding part, which may be arranged on the housing 106. Thus, the first electrode unit 110 may be connected via the connector 120 to components arranged in the housing 106.

The first electrode unit 110 may further comprise fixation structure(s) 122 for fixating the electrode unit 110 in the body of the subject. The first electrode unit 110 may for instance comprise hooks or barbs for allowing the first electrode unit 110 to be fixated in relation to the bone 102. The fixation structure(s) 122 may be provided at an outer surface of the elongate body 112 for allowing the fixation structure(s) 122 to engage with e.g. tissue of the subject. The fixation structure(s) 122 may be configured to directly engage with tissue but may alternatively be configured to be engaged by a suture for fixating the first electrode unit 110 in relation to the bone 102 using suturing.

Referring again to FIG. 1, the device 100 further comprises an injection signal generating unit 150. The injection signal generating unit 150 is configured to output an injection signal to the first and second electrode units 110, 130, for generating the electrical signal between the first electrode area 116 and the second electrode area 136.

The device further comprises a measurement unit 160. The measurement unit 160 is configured to detect a measurement signal induced by the injection signal. The measurement unit 160 may be connected to the first electrode unit 110 and the second electrode unit 130 for detecting the measurement signal. Alternatively, the measurement unit 160 is connected to other electrodes for detecting the measurement signal.

The injection signal may be a current signal or a voltage signal. If a current signal is used for the injection signal, the measurement unit 160 may detect a voltage signal. If a voltage signal is used for the injection signal, the measurement unit 160 may detect a current signal.

The injection signal may be an alternating current (AC) signal. In an embodiment, the AC signal may be varied such that a sequence of a plurality of different frequencies are used in the injection signal. The frequency or frequencies used may be in a range of 1 kHz-1 MHz, such as 1-10 kHz. It should be realized that frequencies may be used at which changes in impedance due to changes in bone density would be detectable.

According to an alternative, the injection signal may be a direct current (DC) signal. Then, a discharging phase may be used in order not to charge tissue between the first and the second electrode areas 116, 136.

A small amplitude of the injection signal may be used such that the injection signal will not cause any sensation or trigger any response in the subject. Rather, the injection signal should only be used for measuring the impedance between the first electrode area 116 and the second electrode area 136. For instance, the amplitude of the injection signal may be so small that an activation threshold of a nerve is not exceeded.

The measurement signal allows an impedance between the first electrode area 116 and the second electrode area 136 to be determined. The measurement signal may be passed from the measurement unit 160 to a processing unit for allowing impedance to be determined, wherein the impedance corresponds to a ratio of the voltage across the first and the second electrode area 116, 136 and the current between the first and the second electrode area 116, 136. However, it should be realized that the actual impedance need not necessarily be calculated. The measurement signal may be used in itself as a representation of a level of the impedance, such that changes in the impedance may be determined based on the measurement signal alone.

The injection signal generating unit 150 and the measurement unit 160 may be arranged in the housing 106. In fact, all components of the device 100 except the first electrode unit 110 and the second electrode unit 130 may be completely arranged within the housing 106, which facilitates arranging the device 100 in the body of the subject.

The housing 106 may comprise a glass encapsulation. This may protect the components within the housing 106 when implanted in the body of the subject so as to preserve functionality of the device 100 when implanted.

The connector 120 of the first electrode unit 110 and a connector 140 of the second electrode unit 130 may be connected to the housing 106 via a connector block. The connector block may isolate the connectors 120, 140 from each other so as to prevent a current flow between the connectors 120, 140 which would otherwise affect impedance measurements.

The housing 106 may comprise fixation structures 108 for fixating the housing in relation to the target bone 102. The housing 106 may be configured to be implanted in soft tissue next to the target bone 102.

The housing 106 may for instance comprise hooks or barbs for allowing the housing 106 to be fixated in relation to the target bone 102. The fixation structure(s) 108 may be provided at an external wall of the housing 106 for allowing the fixation structure(s) 108 to engage with e.g. tissue of the subject. The fixation structure(s) 108 may be configured to directly engage with tissue but may alternatively be configured to be engaged by a suture for fixating the housing 106 in relation to the bone 102 using suturing. According to yet another alternative, the housing 106 may be configured to be fixated to the target bone 102, e.g. by screws extending into the bone 102. The housing 106 may thus comprise screw holes to allow for screws to engage with the housing 106 before also engaging with the bone 102.

The housing 106, the first electrode unit 110, and the second electrode unit 130 may be completely arranged in the body of the subject so that the device 100 is configured to be fully implanted in the subject. This allows for the device 100 to be permanently arranged in the subject to facilitate continuous monitoring of bone density. However, it should be realized that the entire device 100 need not necessarily be implanted, such that some component(s) of the device 100, such as a processing unit which may be connected through wire or wirelessly to other components of the device, may be e.g. mounted at the skin of the subject close to the target bone 102.

Figure 3:
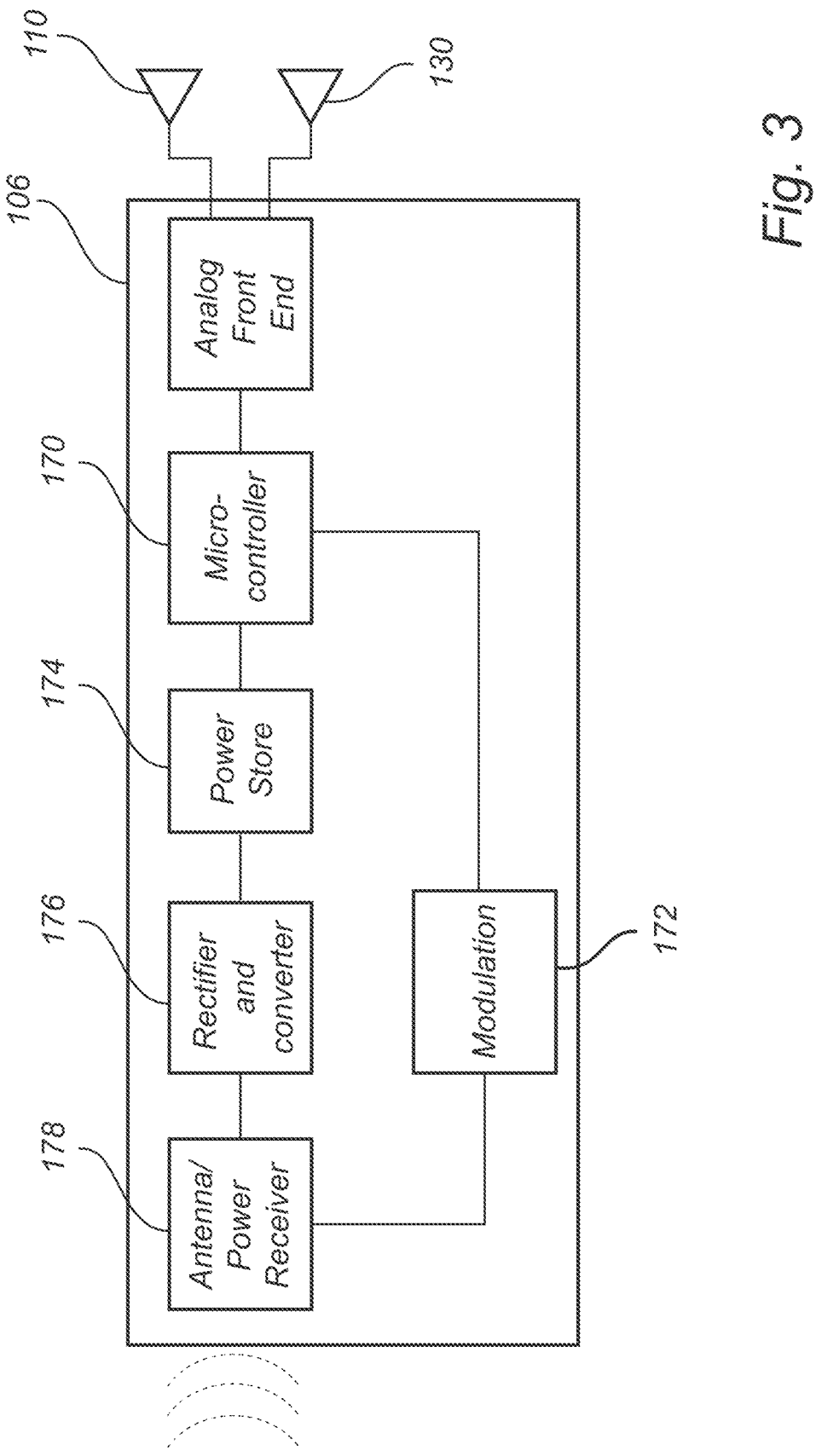
FIG. 3 is a schematic view of internal component within a housing of the device.

Referring now to FIG. 3, functionality of components within the housing 102 is further described.

As shown in FIG. 3, the device 100 may comprise an analog front end, which is connected to the first and the second electrode units 110, 130. The analog front end may comprise the injection signal generating unit 150 for generating the injection signal and the measurement unit 160 for detecting the measurement signal.

The analog front end may be connected to a microcontroller 170, which may be configured to control functionality of the device 100. The microcontroller 170 may comprise a processing unit, and a memory. As an alternative to a microcontroller, the device 100 may comprise any type of processing unit, such as a central processing unit (CPU), and a memory connected thereto.

The microcontroller 170 may be configured to control the injection signal generating unit 150 and the measurement unit 160. Thus, the microcontroller 170 may for instance transmit trigger signals for triggering the injection signal generating unit 150 to output the injection signal and the measurement unit 160 to acquire the measurement signal.

The microcontroller 170 may further be configured to receive the measurement signals from the measurement unit 160 and to process the measurement signals. The microcontroller 170 may process the measurement signals to determine the impedance for the subject and may further process the determined impedance to assess bone density of the subject.

For instance, the microcontroller 170 may store historical measurement results of the impedance of the subject. The microcontroller 170 may then compare measurement results to the historical measurement results. Based on such comparison, the microcontroller 170 may identify a change in the determined impedance for the subject. For instance, a change may be identified if a deviation of the measurement result from the historical measurement results exceeds a set threshold.

The microcontroller 170 may be configured to generate an alert message if the deviation exceeds the set threshold, so as to indicate that there may be a need for further investigation of a condition of the subject.

According to another embodiment, the microcontroller 170 may be configured to store nominal measurement results of the impedance, wherein the nominal measurement results may apply generally to a population. The microcontroller 170 may then compare measurement results to the nominal measurement results. Based on such comparison, the microcontroller 170 may identify a deviation in the determined impedance for the subject compared to nominal results. The microcontroller 170 may be configured to generate an alert message based on the deviation, so as to indicate that there may be a need for further investigation of a condition of the subject.

The microcontroller 170 may further store a unique identifier related to the subject in which the device 100 is used. The unique identifier may be pulled from the microcontroller 170 to allow identification of the subject and allow pulling medical history from a medical database. This may be used e.g. in an emergency situation, when the subject may be unconscious, in order to pull medical history to ensure that the subject is given correct treatment.

The device 100 may further comprise an antenna 178, which may be used for communication with an external unit and/or for receiving power for powering the device 100. Communication with the external unit and power transfer may be performed by the same unit. However, alternatively, different units are used for communication and for power transfer.

Both communication with the external unit and power transfer may be provided wirelessly. This implies that communication and power transfer is enabled even if the device 100 is fully implanted.

The power transfer mechanism may for instance be provided by inductive coupling, by capacitive coupling or through ultrasonic power or another mechanical wave or through an optical signal or another electromagnetic signal.

The communication may for instance be provided by wireless radio telecommunication, by a load modulation mechanism, such as used in radio frequency identification (RFID) communication, or through modulating scattered mechanical waves or the optical signal or another electromagnetic signal.

The microcontroller 170 may be configured to communicate with an external unit via the antenna 178. The microcontroller 170 may thus transmit and receive signals via a modulation unit 172 for extracting information from a received signal or modulating a signal to be transmitted by the antenna 178.

The antenna 178 may further be connected to a rectifier and converter 176 for providing a power supply based on received power by the antenna 178. The rectifier and converter 176 may further be connected to a power store 174, which may be configured to momentarily store power for powering the device 100.

The device 100 may be powered by external powering, such that the device 100 has no internal power source. This may be advantageous for a device 100 that is to be implanted for a long period of time, as the device 100 may maintain functionality so as to make the device 100 permanent.

According to an alternative, the device 100 may comprise a rechargeable battery, which may provide power to the device 100. Thus, the device 100 would not be dependent on external powering in order to perform measurements, but the device 100 would need to receive power from time to time for recharging the battery.

Figure 4:
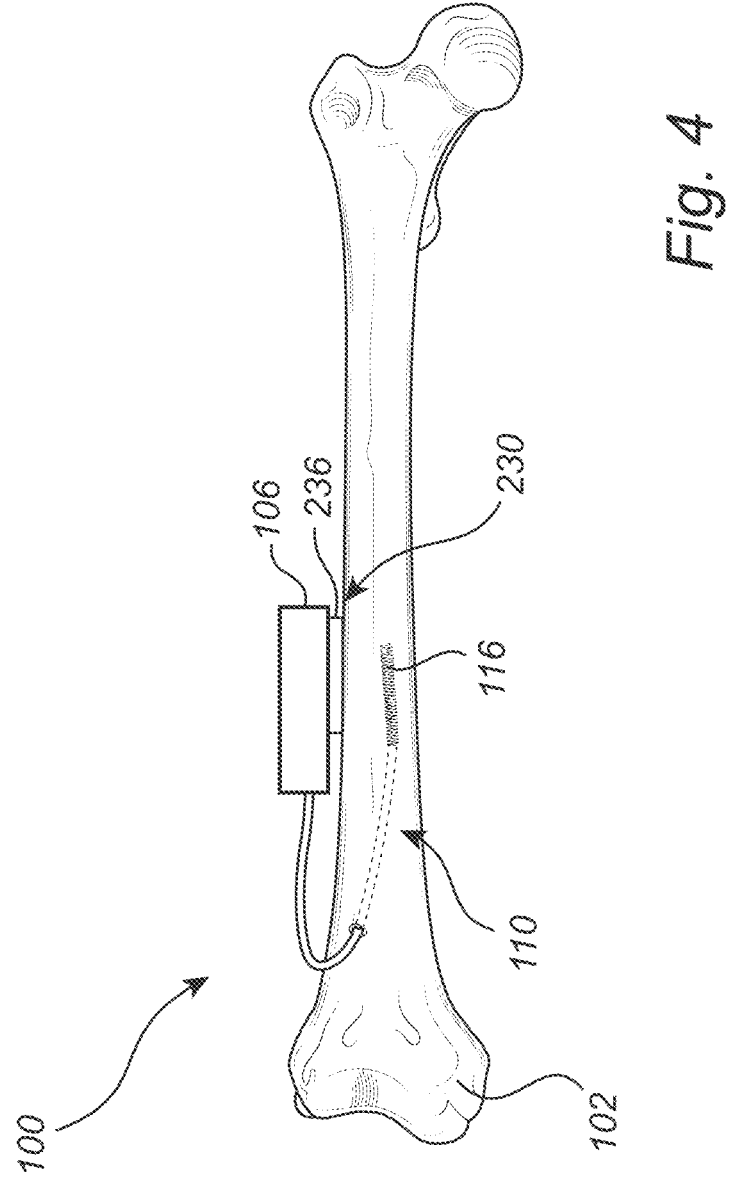
FIG. 4 is a schematic view of a device according to another embodiment.

Referring now to FIG. 4, an alternative embodiment of the second electrode unit 230 will be described.

As shown in FIG. 4, the second electrode unit 230 may be mounted on an external wall of the housing 106 of the device 100, such that a conductive material is arranged on the external wall for defining the second electrode area 236.

Hence, the second electrode area 236 may be arranged directly on the housing. This implies that the second electrode area 236 need not be separately positioned in the subject but may rather be arranged in a proper position when the housing 106 is positioned in the subject. Further, there is no need of connecting the second electrode unit 230 to the housing 106 during implantation of the device 100. Rather, the second electrode unit 230 may be mounted on the housing 106 during manufacture of the device 100.

Figure 5:
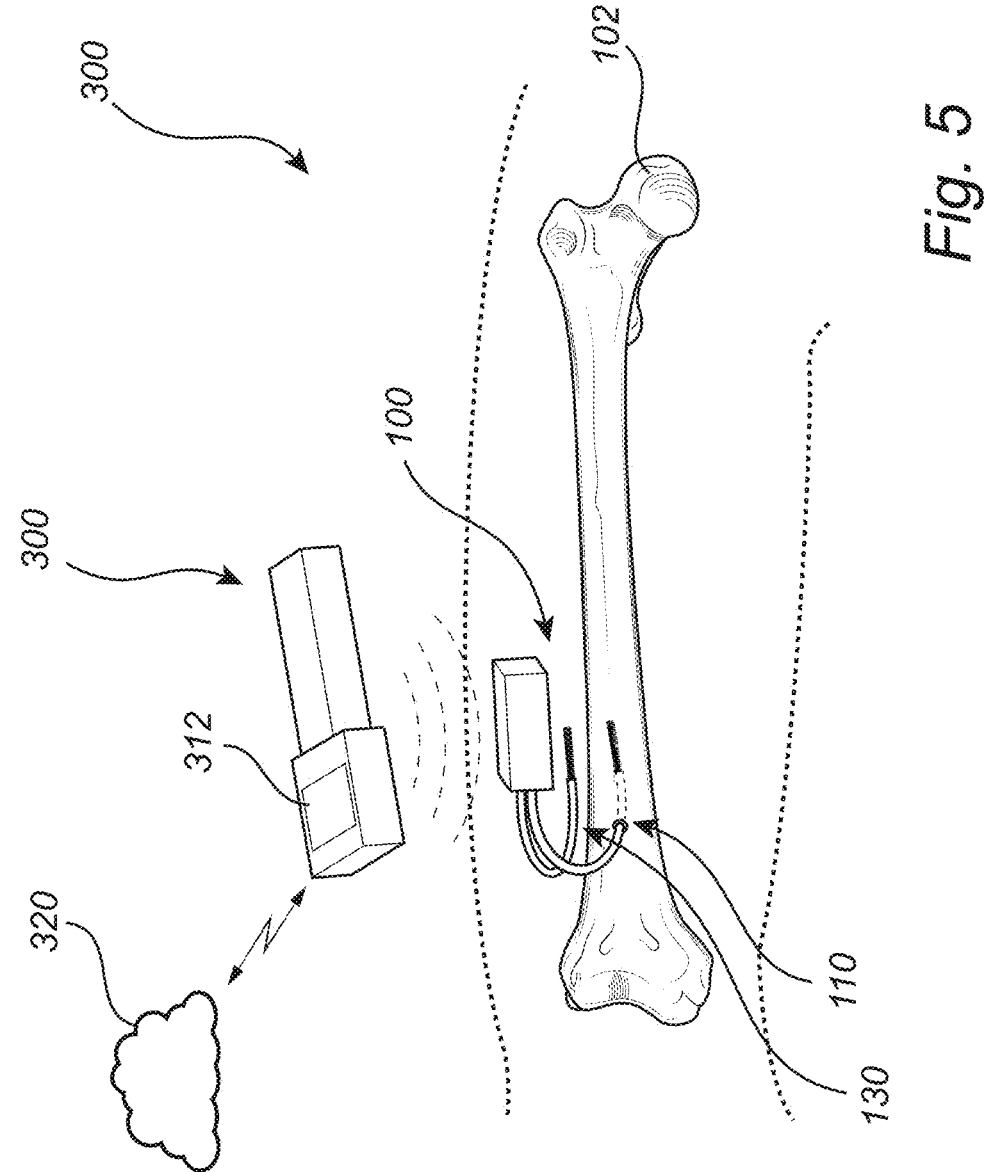
FIG. 5 is a schematic view of a system according to an embodiment.

Referring now to FIG. 5, a system 300 for monitoring bone density will be further described. The system 300 includes a device 100 according to any of the embodiments described above, wherein the device 100 is configured to be fully implanted in the subject.

The system 300 further comprises a dedicated external reader unit 310 for communicating with the device 100. Thanks to having a dedicated external reader unit 310, the system 300 may be properly set up to ensure a robust functionality of the system 300. However, it should be realized that the device 100 may be configured such that a dedicated external reader unit may not be necessarily used for communicating with the device 100. Rather, the device 100 may for instance be configured to communicate with a smart phone or another external unit which may have capability to communicate wirelessly with the device 100.

The external reader unit 310 is configured to provide external powering of the device 100 that is implanted in the subject. The external reader unit 310 is further configured for wireless communication with the device 100, such that the external reader unit 310 may receive measurement results from the device 100.

The external reader unit 310 may comprise circuitry for enabling powering of the device 100. The external reader unit 310 may thus comprise a circuitry for providing inductive or capacitive coupling to the device 100 for wireless power transfer to the device 100. The external reader unit 310 may alternatively be configured to emit an electromagnetic wave, such as a light wave for optical energy transfer, or a radio frequency wave for power transfer. As yet another alternative, the external reader unit 310 may be configured to emit a mechanical wave, such as an ultrasonic wave, for power transfer.

The external reader unit 310 is further configured to at least receive communication signals through wireless communication with the device 100. The wireless communication with the device 100 may use the same technology as wireless power transfer. However, the wireless communication and wireless power transfer may alternatively use separate circuitries.

The wireless communication may for instance be performed through wireless radio telecommunication, through radio frequency identification (RFID) communication, through modulating of scattered waves, such as mechanical waves, or through optical communication.

The subject may control operation of the device 100 through the external reader unit 310. For instance, the subject may initiate measurements by using the external reader unit 310 to power the device 100 and trigger a new measurement to be performed. The external reader unit 310 may be handheld such that the subject may easily handle the external reader unit 310 and bring the external reader unit 310 in sufficient vicinity to the device 100 for wireless power transfer to the device 100. For instance, the external reader unit 310 may be held at the skin where the device 100 is implanted for wireless power transfer from the external reader unit 310 to the device 100.

When the device 100 is powered, the device 100 may initiate a new measurement to be performed, determine measurement results, possibly process the measurement results, and then communicate the measurement results to the external reader unit 310. The external reader unit 310 may further comprise a processing unit for processing of received measurement results, e.g. for further analysis of the measurement results.

The external reader unit 310 comprises a user interface 312 comprising a display to allow measurement results to be presented to the subject. The subject may thus be presented with actual measurement results each time a measurement is performed. However, the external reader unit 310 may also be configured to present historical measurement results to allow any changes in impedance as a measure of bone density to be followed by the subject. Also, the external reader unit 310 may be configured to provide particular output, such as a blinking on the display or a sound signal, if a measurement result triggers an alert message providing an indication of a deterioration of bone density such that further action may be necessary.

The user interface 312 may further enable the subject to provide input for controlling the external reader unit 310 and/or the device 100. For instance, the user interface 312 may provide a possibility for the subject to control wireless power transfer to the device 100 for triggering an impedance measurement to be performed.

The external reader unit 310 may further be configured to communicate with a remote unit 320. The external reader unit 310 may thus function as a gateway or a local radio gateway. This may for instance be used to allow acquired measurement results to be offloaded from the external reader unit 310 to the remote unit 310 for further analysis therein. The remote unit 320 may be configured to analyze or present measurement results to allow long term changes or trends of the bone density to be monitored. For instance, the remote unit 320 may be a computer system of a hospital, to allow a physician responsible for treatment of the subject to follow progress of bone density.

The external reader unit 310 may also or alternatively be configured to communicate with a local unit, which may be in the subject's home, such as a smart phone. For instance, the external reader unit 310 may have minimum functionality and merely be configured to provide wireless power transfer and wireless communication with the device 100. Any communication from the device 100 may be forwarded to the local unit, which may provide a display for presentation of measurement results and/or a user interface for providing control signals to be transmitted to the external reader unit 310 and further to the device 100.

It should be realized that processing of measurement results may take place in the device 100, the external reader unit 310, the local unit or the remote unit 320. Further, processing of measurement results may be distributed between these units or may be entirely performed in one unit.

The system 300 allows continuous monitoring of bone density over a long period of time. The monitoring of bone density may be performed in home environment of the subject, such that the subject need not visit a hospital for screening of osteoporosis. Thus, the use of the system 300 may eliminate a need for CT or X-ray scans for screening of osteoporosis. However, it should be realized that the system 300 using impedance measurement as a measure of bone density may be used as a complement to CT or X-ray scans, such that measurement results from the system 300 may be used for scheduling further investigation. This may still be used for reducing frequency of CT or X-ray scans.

The system 300 may be used for monitoring bone density as a feedback on treatment of osteoporosis. For instance, diet and lifestyle of the subject as well as drugs may affect bone density. Thus, the treatment of osteoporosis may be based on a combination of actions. The monitoring of bone density may be used for providing feedback on the efficiency of treatment to allow changing or adjusting the treatment based on the feedback. The external reader unit 310 may also provide guidance through the user interface 312 to the subject for ensuring that desired diet and lifestyle is followed by the subject.

Figure 6:
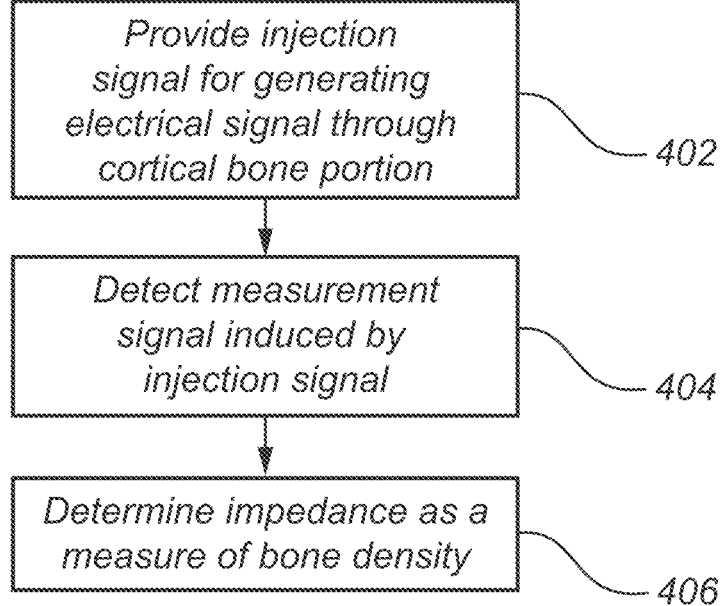
FIG. 6 is a flow chart of a method according to an embodiment.

Referring now to FIG. 6, a method for monitoring bone density using the device 100 will be briefly described.

The method comprises providing 402 an injection signal for generating an electrical signal between the first electrode area 116 and the second electrode area 136, 236. The first electrode area 116 may be arranged inside or within a cortical bone of the target bone 102 of the subject, and the second electrode area 136, 236 may be arranged outside the target bone 102. The first electrode area 116 and the second electrode area 136, 236 are thus arranged in relation to the cortical bone portion 104 of the bone 102 such that the electrical signal between the first electrode area 116 and the second electrode area 136, 236 travels through the cortical bone portion 104 of the bone 102.

The method further comprises detecting 404 a measurement signal induced by the injection signal. The measurement signal may be measured between the first electrode area 116 and the second electrode area 136, 236 or using separate electrodes. The injection signal may be a current signal or a voltage signal. If a current signal is used for the injection signal, a voltage signal may be detected by the measurement signal. If a voltage signal is used for the injection signal, a current signal may be detected by the measurement signal.

The method further comprises determining 406 an impedance between the first electrode area 116 and the second electrode area 136, 236 as a measure of bone density.

The method may be performed in the device 100 being fully implanted in the subject. The method thus facilitates monitoring of bone density in home environment of the subject.

The method may further comprise communicating a measurement result based on the determined impedance from the device 100 to an external reader unit 310. The communicated measurement result may then be further processed and/or displayed to the subject.

Referring now to FIGS. 7a-7g, a method for implanting the device 100 for monitoring bone density will be described.

The method requires access to internal parts of the body of the subject in which the device 100 is to be implanted. Such access may be acquired through minimally invasive techniques and/or through open surgery.

Figure 7A:
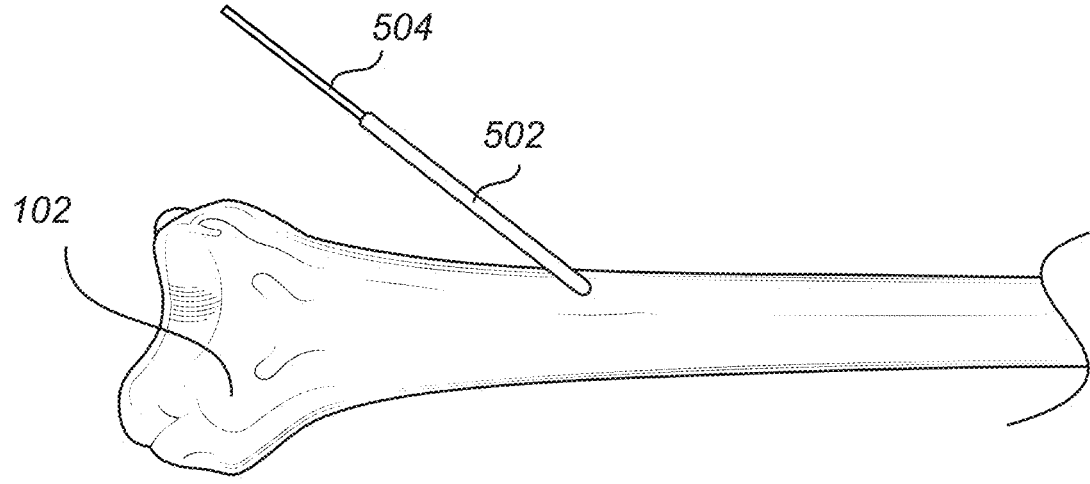
FIGS. 7a-7g are schematic views illustrating steps in a method for implanting a device.

As shown in FIG. 7a, a guide 502 may be advanced to a target position of the target bone 102, where access into the target bone 102 is to be acquired. The guide 502 may allow a tool 504 to be guided to the target position for providing access into the target bone 102.

Figure 7B:
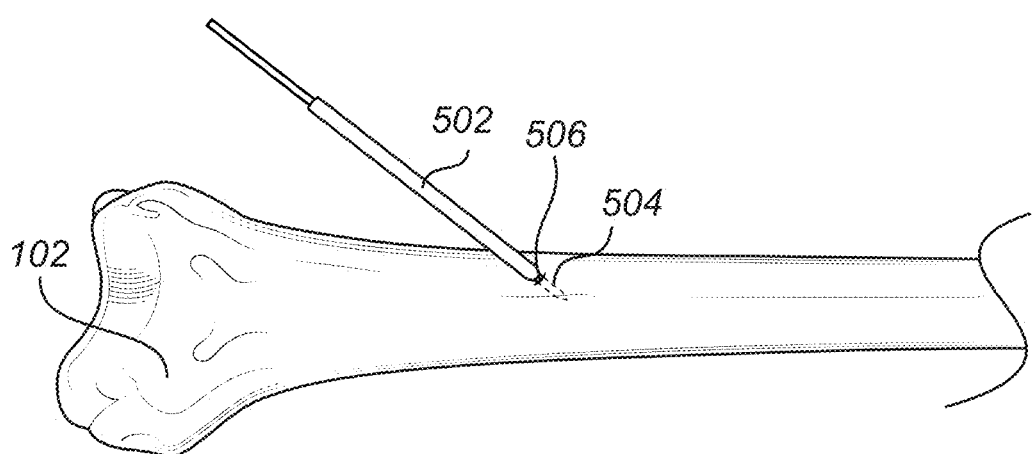

As shown in FIG. 7b, the method comprises acquiring access to the interior of the bone 102. This may be achieved by drilling into the bone 102 to form an opening 506 through the surface of the bone 102 to allow access into the interior of the bone 102. The opening 506 may extend through the cortical bone of the bone 102 to provide access into the interior of the bone 102 inside the cortical bone. It should be realized that access to the interior of the bone 102 need not necessarily be performed by drilling or not even necessarily through mechanical manipulation of the bone 102 but any other manner for forming an opening 504 into the bone 102 may be used.

Figure 7C:
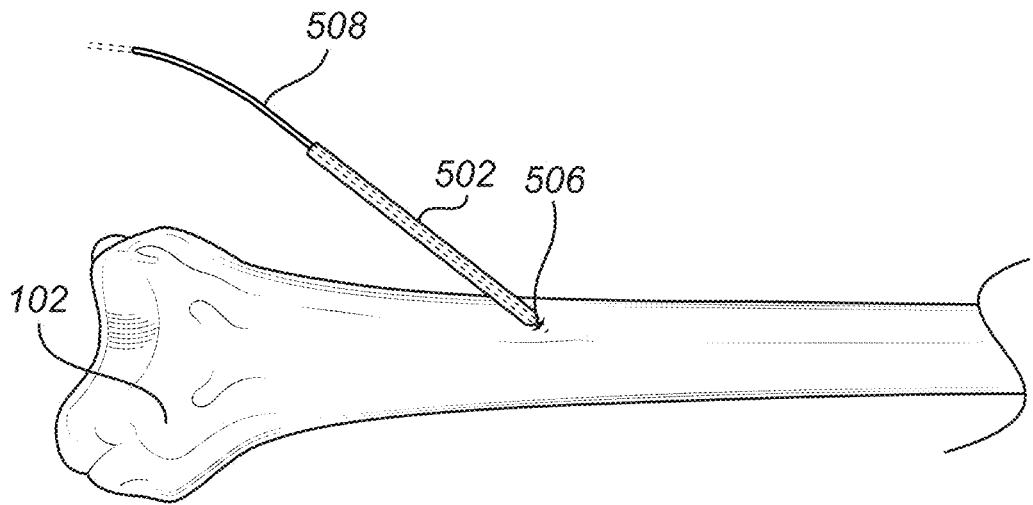
Figure 7D:
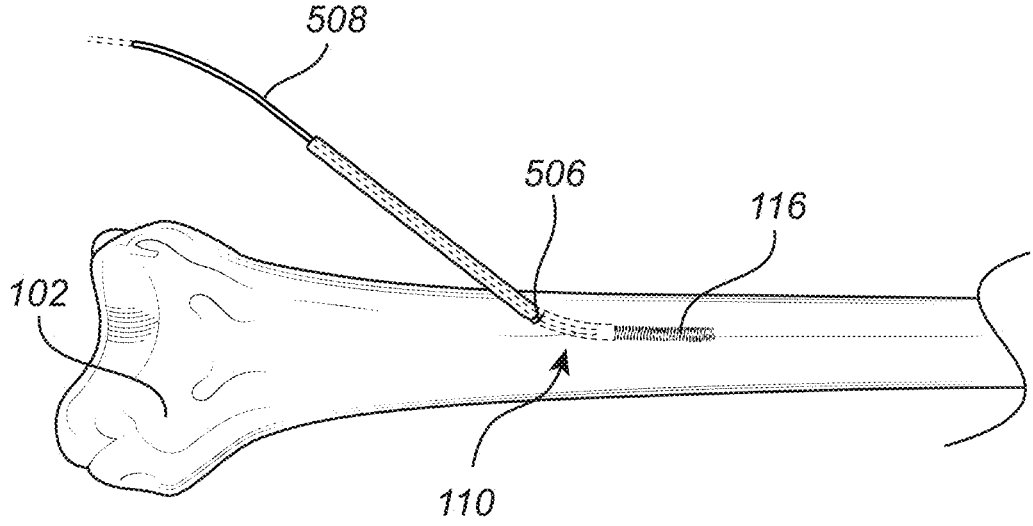

As shown in FIGS. 7c-d, a guide wire 508 may then be guided through the guide 502, through the opening 506 into the interior of the bone 102. The guide wire 508 may be inserted into the bone 102 to extend along the bone 102 such that an end of the guide wire 508 is arranged at a distance from the opening 506.

As further shown in FIG. 7d, the first electrode unit 110 may then be guided along the guide wire 508 so as to guide the first electrode area 116 into position in the interior of the bone 102. The first electrode area 16 may thus be arranged in the bone 102. The guide wire 508 may then be removed leaving the first electrode unit 110 in the body of the subject with the first electrode area 116 in position.

Before or after the guide wire 508 is removed, the first electrode unit 110 may be fixated to the bone 102 for fixating the position of the first electrode area 116 inside the bone 102. The first electrode unit 110 may for instance be fixated to the bone 102 at the opening 506. The first electrode unit 110 may be fixated using a fixation structure that may engage with the bone 102 or tissue around the bone 102. The first electrode unit 110 may alternatively be fixated through suturing.

Figure 7E:
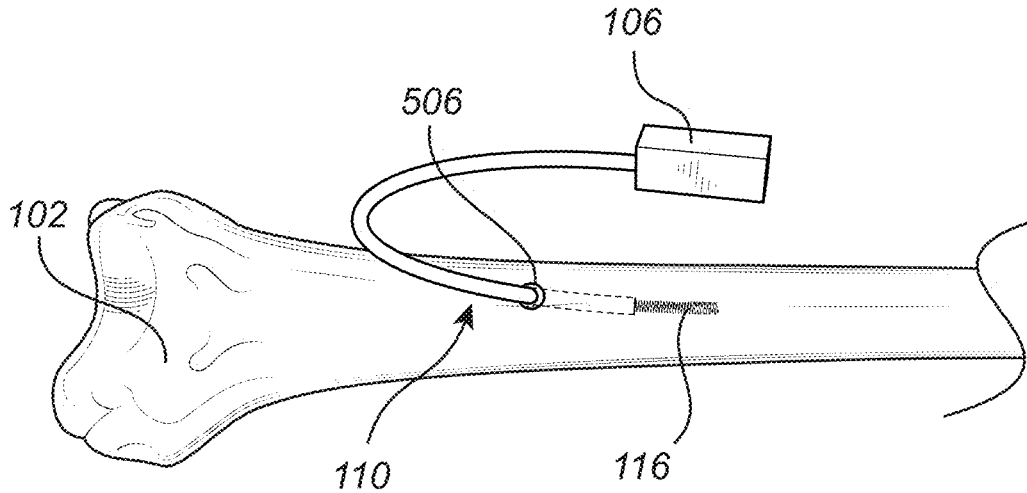

As shown in FIG. 7e, the housing 106 of the device 100 may be inserted into the body of the subject such that the device 100 is arranged in a desired position in vicinity of the bone 102. The housing 106 of the device 100 may be inserted through a guide hole for minimally invasive insertion of the housing 106, but the housing 106 of the device 100 may alternatively be inserted through open surgery.

The housing 106 may be fixated in the desired position. This may be achieved by arranging fixation structures on the housing 106 to directly engage with the bone 102 or soft tissue next to the bone 102. According to an alternative, the housing 106 may be fixated through suturing. According to yet another alternative, the housing 106 may be fixated to the bone 102, e.g. by using screws engaging with the housing 106 to further extend into the bone 102.

As further shown in FIG. 7e, the first electrode unit 110 may be connected to the housing 106. This may be achieved by grabbing an end of the first electrode unit 110 for carrying the connector 120 to the housing 106. For instance, a tube, possibly with a needle at an end of the tube, may be used for carrying the end of the first electrode unit 110 towards the housing 106 so as to tunnel the connector 120 to the housing 106. Once in position, the connector 120 may be connected to a corresponding part on the housing 106. It should also be realized that the first electrode unit 110 may be fixated in the body of the subject after the first electrode unit 110 has been connected to the housing 106.

According to an alternative, the first electrode unit 110 may be pre-connected to the housing 106 before the housing 106 is inserted into the body of the subject. In such case, when the housing 106 has been arranged in position in vicinity of the bone 102, the first electrode unit 110 may be grabbed for guiding the tip 118 of the first electrode unit 110 with the first electrode area 116 to the opening 506 into the bone and further to arrange the first electrode area 116 in the desired position inside or within the cortical bone portion of the bone 102.

The method further comprises arranging the second electrode area 136, 236 of the second electrode unit 130, 230 outside the bone. The second electrode area 136, 236 is arranged in relation to the first electrode area 116 such that an electrical signal between the first electrode area 116 and

Figure 7F:
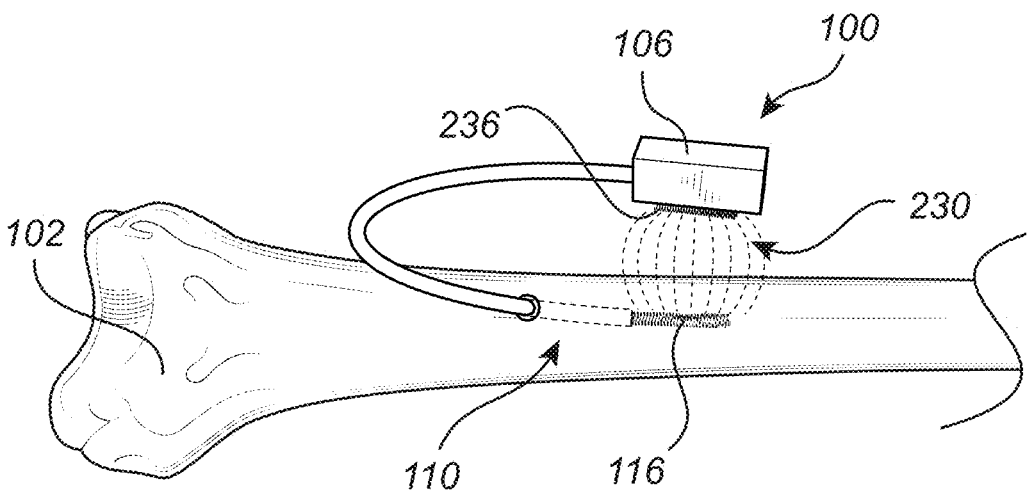
Figure 7G:
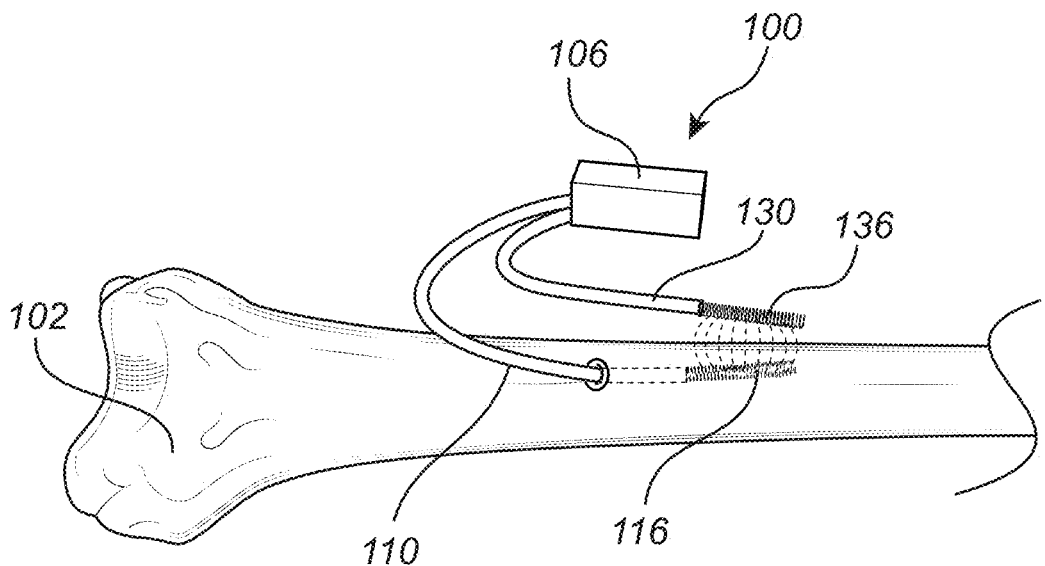

20 the second electrode area 136, 236 will travel through the cortical bone portion of the bone 104. Referring now to FIGS. 7f-7g, two alternative ways for arranging the second electrode area 136, 236 in the body of the subject are discussed.

As shown in FIG. 7f, the second electrode area 236 of the second electrode unit 230 may be arranged on an external wall of the housing 100. Thus, when the housing 106 is inserted into the body of the subject, the housing 100 will carry the second electrode area 236 so as to simultaneously arrange the second electrode area 236 outside the bone 102. The housing 106 is arranged in the body of the subject such that the second electrode area 236 is positioned in relation to the first electrode area 116 such that an electrical signal between the first electrode area 116 and the second electrode area 236 travels through the cortical bone portion of the bone 102.

As shown in FIG. 7g, the second electrode unit 130 may be connected to the housing 106 in a similar manner as the first electrode unit 110. The second electrode unit 130 may be pre-connected to the housing 106 before the housing 106 is inserted into the body of the subject. In such case, when the housing 106 has been arranged in position in vicinity of the bone 102, the second electrode unit 130 may be grabbed for guiding the tip of the second electrode unit 110 with the second electrode area 136 to arrange the second electrode area 136 in the desired position outside the bone 102.

Alternatively, the second electrode unit 130 may be inserted into the body of the subject separately from the housing 106. The second electrode unit 130 may be inserted by being guided on a guide wire, wherein the second electrode area 136 may be guided to arrange the second electrode area 136 in the desired position outside the bone 102. The guide wire 508 may then be removed leaving the second electrode unit 130 in the body of the subject with second electrode area 136 in position.

Before or after the guide wire is removed, the second electrode unit 130 may be fixated to the bone 102 for fixating the position of the second electrode area 136 outside the bone 102. The second electrode unit 130 may be fixated using a fixation structure that may engage with the bone 102 or tissue around the bone 102. The second electrode unit 130 may alternatively be fixated through suturing.

The second electrode unit 130 may further be connected to the housing 106. This may be achieved by grabbing an end of the second electrode unit 130 for carrying the connector to the housing 106. For instance, a tube, possibly with a needle at an end of the tube, may be used for carrying the end of the second electrode unit 130 towards the housing 106 so as to tunnel the connector to the housing 106. Once in position, the connector may be connected to a corresponding part on the housing 106. It should also be realized that the second electrode unit 130 may be fixated in the body of the subject after the second electrode unit 130 has been connected to the housing 106.

When the housing 106, the first electrode unit 110 and the second electrode unit 130, 230 have all been positioned correctly in the body of the subject, all cuts and incisions are closed leaving the device 100 implanted in the body of the subject.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for monitoring bone density, said method comprising:

providing an injection signal for generating an electrical signal between a first electrode area and a second electrode area, wherein the first electrode area and the second electrode area are arranged in relation to a cortical bone portion of a bone such that the electrical signal between the first electrode area and the second electrode area travels through the cortical bone portion of the bone, wherein the first electrode area is arranged on an inside of the cortical bone portion and the second electrode area is arranged outside the bone;

detecting a measurement signal induced by the injection signal; and determining an impedance between the first electrode area and the second electrode area as a measure of bone density, wherein the first electrode area is arranged on a tip of a flexible elongate body, wherein the flexible elongate body is configured to guide the tip at the inside of the cortical bone portion.

2. The method according to claim 1, further comprising arranging the first electrode area within the bone and arranging the second electrode area outside the bone.

3. The method according to claim 2, further comprising performing the providing of the injection signal by an injection signal generating unit and performing the detecting of the measurement signal by a measurement unit, wherein the injection signal generating unit and the measurement unit are provided in a housing.

4. The method according to claim 3, wherein arranging the first electrode area within the bone comprises arranging a first electrode unit comprising an elongate body extending from the housing with a tip of the elongate body exposing a conductive portion forming the first electrode area.

5. The method according to claim 4, wherein the tip has a directional shape for promoting the electrical signal being directed towards or being received from the second electrode area.

6. The method according to claim 4, wherein the housing and the first electrode unit each is fixated by fixation structures in relation to the bone.

7. The method according to claim 4, wherein arranging the first electrode unit comprises acquiring access to an interior of a bone, and guiding the first electrode area of the first electrode unit at the tip of the first electrode unit into the interior of the bone for arranging the first electrode area of the first electrode unit on an inside of the cortical bone portion.

8. The method according to claim 3, wherein arranging the second electrode area outside the bone comprises arranging a second electrode unit comprising an elongate body extending from the housing with a tip of the elongate body exposing a conductive portion forming the second electrode area or providing a conductive portion arranged on an external wall of the housing for forming the second electrode area.

9. The method according to claim 3, further comprising powering the injection signal generation unit and the measurement unit through wireless power transfer.

10. The method according to claim 1, further comprising implanting a device for monitoring bone density in a subject.

11. The method according to claim 1, further comprising communicating measurement results to an external unit through wireless communication.

12. The method according to claim 1, wherein providing the injection signal comprises providing at least one alternating current (AC) signal of one or more frequencies and/or a direct current (DC) signal.

13. The method according to claim 1, further comprising storing historical measurement results of the impedance of a subject and comparing measurement results to the historical measurement results for identifying a change in the determined impedance for the subject.

14. The method according to claim 1, further comprising processing the determined impedance for determining whether a subject suffers from osteoporosis.

* * * * *